United States Patent [19]

Labesque et al.

[11] Patent Number: 4,911,849

[45] Date of Patent: Mar. 27, 1990

[54] METHOD AND MEANS OF AERATION-POWERED WATER FLOW USING FOIL-SHAPED CONTOUR

[75] Inventors: Serge Labesque, Glen Ellen; Benjamin R. Roberts, Los Altos, both of Calif.

[73] Assignees: William Kreysler & Associates, Inc., Penngrove; Ocean Genetics, Inc., Santa Cruz, both of Calif.

[21] Appl. No.: 214,691

[22] Filed: Jun. 30, 1988

[51] Int. Cl.$^4$ .............................................. C02F 7/00
[52] U.S. Cl. .................................... 210/747; 210/169; 210/170; 210/199; 210/221.2; 210/150; 119/3; 261/124; 405/22; 405/62
[58] Field of Search ............... 210/747, 758, 199, 220, 210/169, 170, 221.2, 150, 151; 405/22, 62; 119/3, 5; 261/124

[56] References Cited

U.S. PATENT DOCUMENTS

| | | | |
|---|---|---|---|
| 3,169,921 | 2/1965 | Griffith | 210/747 |
| 3,720,318 | 3/1973 | Cohen | 210/169 |
| 3,850,806 | 11/1974 | Cohen | 210/169 |
| 3,884,810 | 5/1975 | Smyrnow | 210/170 |
| 3,925,522 | 12/1975 | Schreiber | 210/220 |

Primary Examiner—Richard V. Fisher
Assistant Examiner—Cynthia L. Nessler
Attorney, Agent, or Firm—Townsend and Townsend

[57] ABSTRACT

A pump driven by air only is disclosed for providing simultaneous aeration and flow at right angles to the rising air. The pump produces in a shallow tank particle-suspending turbulence which is particularly useful for growth of marine organisms in a sun-exposed tank confined shallow brine solution. The pump is preferably installed in a rectangular tank divided by a baffle between the two tank side walls. The baffle extends parallel to the major axes of the rectangle and stops short of both tank end walls. The fluid is pumped around this baffle in an oval flow pattern. On the shallow bottom of the tank on both sides of the baffle, there is a repeating foil shaped bottom with a manifold for discharging air. The foils of the bottom are generated at right angles to the baffle and oriented from leading edge to trailing edge in the direction of intended fluid rotation around the baffle in the tank. Air is pumped and discharged from the manifold in a rising curtain. As the curtain of air rises, it is entrains a rising wall of water. At the surface, the entrained wall of water circulates into divided flows overlying and normal to the manifolds; one flow is a translational pumping flow passing over the leading edge of the foil and the other is a conventional back eddy.

4 Claims, 2 Drawing Sheets

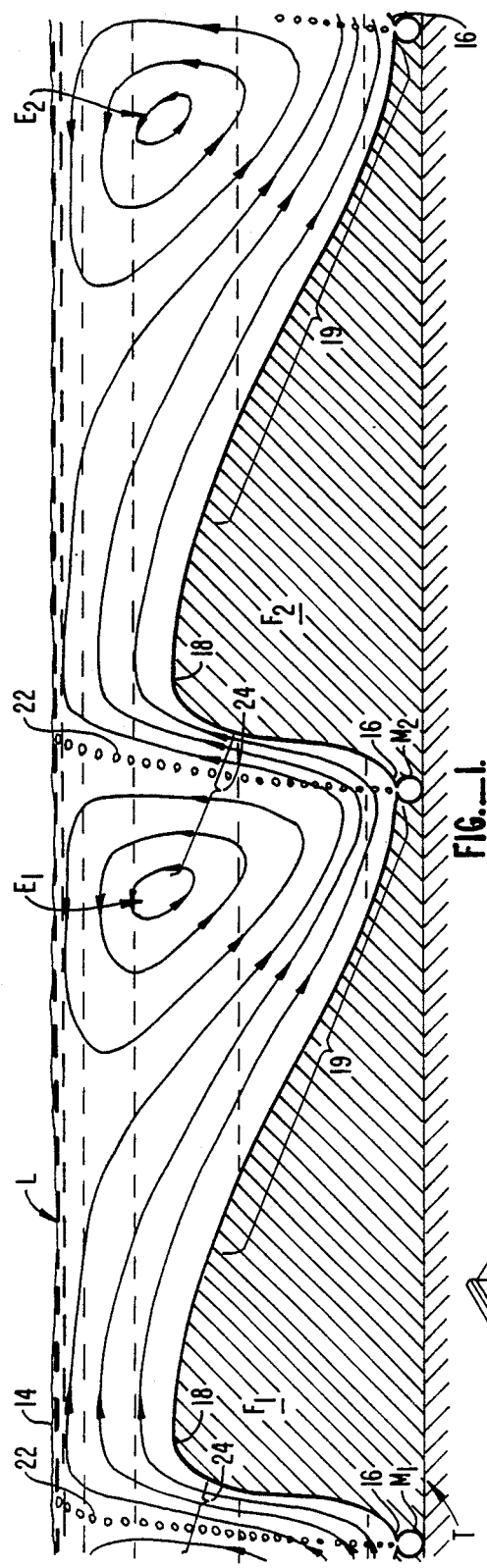
FIG._1.
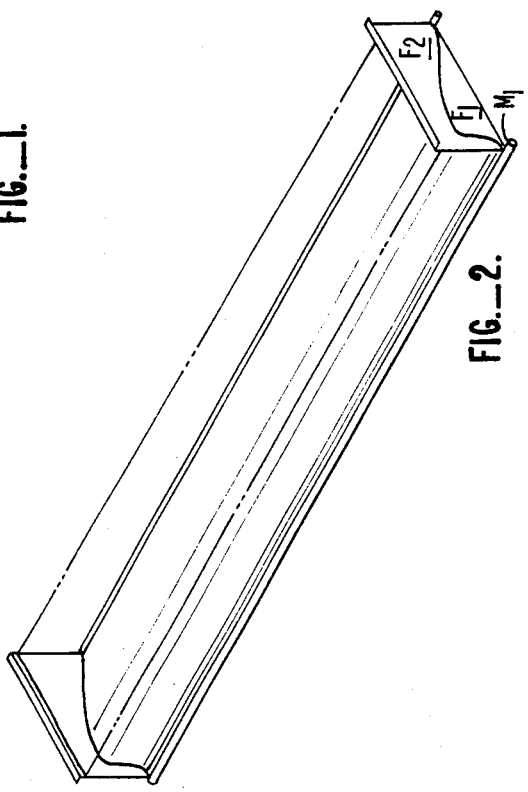
FIG._2.

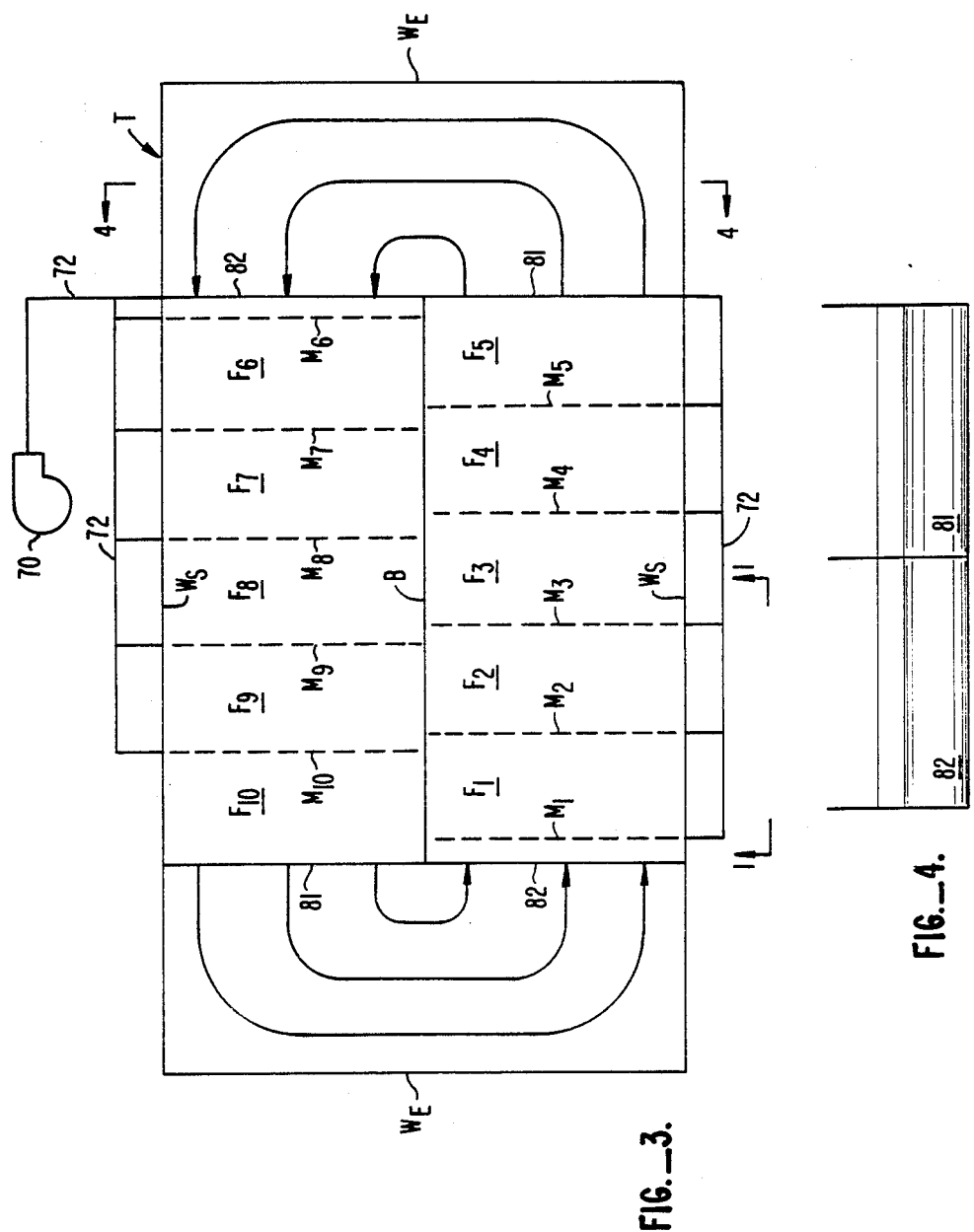

METHOD AND MEANS OF AERATION-POWERED WATER FLOW USING FOIL-SHAPED CONTOUR

This invention relates to an apparatus for simultaneously aerating fluid in a shallow tank as well as pumping the fluid around the tank. More specifically, an air pump is disclosed which produces both aeration and required pumping.

SUMMARY OF THE PRIOR ART

Tanks for the circulation of aerated fluids typically include two pumping components. The first pumping component is for pumping a rising stream of air somewhere in the tank. This rising stream of air accomplishes the desired aeration.

The second component is a pump. The pump effects circulation of the tank so that among other things, a uniform mixture is maintained throughout the solution. For example, by pumping the fluid in a tank by a manifold effecting the desired aeration, a more or less uniform level of aeration can be maintained in the entire fluid mixture within the tank. Similarly, such pumping enables the introduction and withdrawal of materials from fixed points in the circulating tank.

The utility of such tanks can be divided into two general classes. First, many treatment processes require circulation with aeration. An example of such required circulation with aeration is fluids treated within sewage treatment plants.

Secondly, such tanks can be used for the photosynthetic growth of marine organisms. In this case, the flow and aeration maintains the plants uniformly distributed throughout the tank. At the same time, the plants are maintained in an aerated condition required for growth. Moreover, both the pumping and the aeration contribute to the plants being cycled into and out of sunlight for inducing required growth.

SUMMARY OF THE INVENTION

A pump driven by air only is disclosed for providing simultaneous aeration and flow at right angles to the rising air. The pump produces in a shallow tank particle-suspending turbulence which is particularly useful for growth of marine organisms in a sun-exposed tank confined shallow brine solution. The pump is preferably installed in a rectangular tank divided by a baffle between the two tank side walls. The baffle extends parallel to the major axes of the rectangle and stops short of both tank end walls. The fluid is pumped around this baffle in an oval flow pattern. On the shallow bottom of the tank on both sides of the baffle, there is a repeating foil shaped bottom. The foils of the bottom are generated at right angles to the baffle and oriented from leading edge to trailing edge in the direction of intended fluid rotation around the baffle in the tank. Typically, the foils repeat on six foot centers beginning with a trough defining a deep point in the shallow bottom. followed by an immediate rapid rise in the first one foot to define the shallow leading edge of the foil. This shallow edge of the foil thereafter trails off to the depth of the trough in a gradually sloping bottom in the remaining four feet of each foil. In the trough, an air manifold is placed preferably extending the entire length of the trough between the tank side and baffle. Air is pumped and discharged from the manifold in a rising curtain of air. As the curtain of air rises, it is entrains a rising wall of water. At the surface, the entrained wall of water circulates into divided flows overlying and normal to the manifolds; one flow is a translational pumping flow passing over the leading edge of the foil and the other is a conventional back eddy. At the side of the foil adjacent the leading edge, the translational pumping flow circulates to the side of the manifold and spills over the shallow leading edge of the foil. This shallow leading edge of the foil prevents the water from circulating back upon itself in a conventional eddy. The shallow leading edge effects translation of the water down the elongate trailing edge of the foil either to discharge or the next repeating foil. As the water arrives at an adjacent trough leading to the next repeating foil, this arriving water flows into the back eddy produced by the next manifold, thus contributing further to the intended water momentum. Provision is made for providing the ends of the tank adjacent to the baffle with installed weirs to enable the water flow to turn the corners at the rectangular ends of the tank to acquire an oval flow pattern of substantially uniform velocity.

OTHER OBJECTS, FEATURES AND ADVANTAGES

An object of this invention is to disclose an apparatus and process for pumping liquid over a shallow bottom wherein a rising air stream alone both aerates and pumps. Accordingly, a foil shaped shallow bottom is provided on at least a portion of the tank. This foil shaped shallow bottom includes a deep trough defining the beginning of the foil, a rapid rising and shallow leading edge defining the top of the foil and a gradually sloping and deepening trailing edge defining the surface over which fluid is discharged in a pumping action. An air manifold laid on the tank bottom at the low point of the trough discharges an upward curtain of air. This rising curtain of air entrains an accompanying upwardly rising wall of water. The wall of water reaches the surface and divides into two flows, one flow being a conventional back eddy normal to the manifold and away from the leading edge of the foil and the other flow being a translational pumping flow passing over the leading edge of the foil. The water passes from the leading edge of the foil to the trailing edge of the foil with a pumping motion of the water resulting from the upward air flow.

An advantage of this process and apparatus is that both aeration and pumping are combined.

A further object of this invention is disclosed in combination in a series of two such pumps. According to this aspect of the invention, the shallow bottom of the tank is modified so that the trailing edge of one pump foil discharges its translational pumping flow into the trough and leading foil edge of a sequentially next-in-order manifold and foil pump. This discharge mixes with the downwardly flowing conventional eddy of the next foil pump unit. In such mixing, the conventional eddy is reinforced in its circulation.

An advantage of this series placement of the pumps is that the water flow over the trailing edge of a preceding pump reinforces the conventional eddy of the series connected foil pump. Consequently, the two pumps together in series produce an overall pumping effect that neither pump could maintain alone.

A further advantage of this pump is that it is ideal for solutions in which photosynthetic brine solutions are grown. This pump both enables uniform suspension of the microorganisms as well as uniform mixing of the brine solution. Furthermore, the disclosed pump cycles marine organism towards and away from overlying sunlight. This towards and away circulation from overlying sunlight enables a beneficial photosynthetic cycle within the growing plants to occur. Rapid growth follows. For example, the disclosed pump is especially suitable for the rapid growth of seaweed containing agar.

Yet another object to this invention is to disclose the preferred dimensions of the disclosed pump for use with a brine solution containing densely growing seaweed. According to this aspect, a tank bottom on the order of 2 feet four inches maximum depth is provided with a foil repeating at 6 foot intervals. A rapid rise to the crest of the foil at 10 inches of depth is followed by a gradual drop to the maximum depth at the end of the foil. Preferably, the foil is cut from a material such as foam so that mirror image of the cut can itself be used as an identical outline for a foil.

Other objects, features and advantages of this invention will be more apparent after referring to the following specification.

BRIEF DESCRIPTION OF THE DRAWINGS

FIG. 1 is a side elevation section illustrating a shallow tank bottom having a foil bottom therein and manifold disposed for producing simultaneous aeration and pumping of fluid within the tank:

FIG. 2 is an isometric view of a single foil element, the foil element being cut so that a mirror image of the element may be utilized for additional foil;

FIG. 3 is a plan view of a tank containing this invention, the tank here being rectangular, separated by a central baffle and having an oval shaped flow therein;

FIG. 4 is a side elevation section of a weir taken along lines 4—4 of FIG. 3, the weir being constructed to assist uniform flow at the corners of the tank.

DETAILED DESCRIPTION OF A SPECIFIC EMBODIMENT

Referring to FIG. 1, a section of a tank T is illustrated. Tank T is provided with a series of foils $F_1$, $F_2$. Foils $F_1$, $F_2$ define the shallow bottom of the tank.

The tank confines a liquid L. Preferably, liquid L is a brine solution exposed to sunlight at its upper surface 14 and suspending microorganisms growing in response to photosynthesis such as seaweed for the production of agar.

Each foil F begins at a trough 16. The foil rapidly rises to a shallow leading edge at 18, leading edge 18 defining the shallowest point in the tank. As will be more important, it is the shallow edge 18 which enables the translational pumping.

Thereafter, each foil terminates in a trailing edge, 19. Trailing edge 19 extends from leading edge 18 downwardly to a level equal to that of trough 16. In the case where two foils, $F_1$ and $F_2$, are in series, it can be seen that the foil 19 terminates at the following trough 16 of the next repeating foil. At the bottom of each foil, a manifold $M_1$ is placed for foil $F_1$ and a manifold $M_2$ is placed for foil $F_2$. The manifolds preferably extend the entire width of each foil.

Referring to FIG. 2, a foil $F_1$ is illustrated which foil $F_1$ extends half the width of the tank typically from a baffle B to a side wall Ws (see FIG. 3).

Referring to FIG. 2, it can be seen that a block of material—such as styrofoam—is cut with a cutting apparatus (such as a hot wire) so as to define a foil shape $F_1$. It will be seen that by selecting the block carefully, the mirror image of block waste left defines a foil shape which may be used for the next foil, such as foil $F_2$.

Typically, the foam blocks $F_1$ and $F_2$ are thereafter covered with the water impervious material. For example, a fiber glass layer can be placed over the foam to produce the desired bottom profile.

The reader will understand that the illustrated foam and plastic covering construction does not have to be utilized. For example, concrete and even earth covered with a water impervious barrier could be utilized to form the successive foils $F_1$ and $F_2$ in the shallow bottom.

Having set forth the construction, the process of pumping as well as the pump itself can be described.

Manifold $M_1$ and manifold $M_2$ each emit a rising curtain of air 22 bubbling through the liquid within the tank. The rising curtain of air entrains a rising wall of water 24. This entrained wall of water arises to the surface 14 in the shallow bottom tank.

Presuming that the foils $F_1$ and $F_2$ were not present, one could expect the flow effects on either side of the rising curtain of air to be identical. Specifically, equal and oppositely rotating back eddies would be created on either side of the air curtain.

However, the leading edge 18 of foil $F_1$ and the leading edge 18 of foil $F_2$ prevent such a back eddies from occurring. The water flows over the leading edge 18 of the foil. In such flow, it thereafter passes downwardly along the trailing edge 19. Such passage induces a translational pumping flow of water away from the manifold M to and towards the trailing edge of the foil.

At the same time, it can be seen that a conventional eddy E is formed. Eddy E forms upstream of the translational flow overlying the trailing edge of a preceding foil. For example, eddy $E_1$ overlies trailing edge 19 of foil $F_1$.

A further serendipitous effect is present. Specifically, water flowing down the trailing edge 19 of foil $F_1$ is moving in the same direction as eddy $E_1$ produced by the rising air current 22 from manifold $M_2$. It can thus be seen that the translational flow produced by manifold $M_1$ cooperatively interferes with the back eddy $E_1$ produced by manifold $M_2$. Stated more simply, two foils, $F_1$ and $F_2$, in series with their respective manifolds, $M_1$ and $M_2$, produce a total flow which neither alone can sustain.

Continuing further with FIG. 1, comment can be directed to the use of this apparatus for growing in a brine solution a photosynthetic plant such as sunlight exposed seaweed for the production of agar. It has been found that the suspended seaweed can be pumped and aerated in a dense configuration. Specifically, at eddies $E_1$ and $E_2$, the leaves of the seaweed circulate in the brine solution from a position adjacent to surface 14 to a position adjacent to trough 16. In such circulation, they pass into and out of the sunlight. In such passage into and out of sunlight, the photosynthesis is encouraged. Specifically, it has been found that by the produced cycling herein, accelerated growth of such plants occurs.

Referring to FIG. 3, a rectangular tank is illustrated. Rectangular tank T includes side walls Ws and end walls We.

Baffle B is placed centrally in the tank. Baffle B extends precisely in the middle of and parallel to side walls Ws. Baffle B stops short of the end walls We. By its presence, baffle B confines water flow in the tank to an oval flow pattern. The oval flow pattern here illustrated is a counter-clockwise flow pattern.

Each side of the tank includes 5 foils similar to foils $F_1$ and $F_2$. The foils are in series and each include at the leading end thereof a manifold. The manifolds are labelled $M_1$ and through $M_5$ on one side of the tank and $M_6$ and $M_{10}$ on the opposite side of the tank.

After each manifold there are respective foils. Similarly to the manifolds $M_1$ through $M_5$ on one tank side and manifolds $M_6$ through $M_{10}$ on the other tank side the foils are likewise numbered $F_1$ through $F_5$ on one side and $F_6$ through $F_{10}$ on the other side. It will be observed that on each side of the tank, a series connection is present.

An air pump 70 supplies all of the manifolds through lines 72 with air. Air is provided at a pressure sufficient to enter at the water at the depth of 26 inches.

One problem remains. It has been found that at the ends of the tank, the water flow is uneven as the water turns the corner. Specifically, water passes close to the baffle at high velocity as it exits a series of pumps and passes close to a side wall Ws as it enters a series of pumps. In order to preserve uniform velocity, a weir structure $W_E$ is installed at the end of a tank. Such a structure is shown in FIG. 4 which figure is a section taken along lines 4—4 of FIG. 3.

Specifically, two triangular weir sections 81 and 82 are placed at each end of baffle B. The triangular sections on the exit of the pump is directed with its highest base to and towards the baffle B. The weir 81 tapers down to and towards the side wall $W_s$. On the entrance side to each of the pumps, the weir has its highest portion adjacent the wall Ws. It has its lowest elevation portion adjacent to baffle B. In this configuration, it has been found that the weir blocks voluminous water outflow adjacent the baffle and forces outflowing water to that portion of the pump discharge which is adjacent the wall Ws.

The intake is reversed. Specifically, water intakes in higher volume adjacent baffle B and is retarded in its volume adjacent side wall Ws. It has been found that this weir configuration tends to render uniform the flow in the rectangular tank here shown.

The reader will realize that this pump can be disposed in a number of tank configurations. For instance, the tank could be circular. Likewise, other designs may as well be used to render the flow more uniform throughout the tank.

The dimensions here given are exemplary and for preferable use in a brine exposed tank having seaweed growing therein. The reader will understand that the dimensions herein will have to change in accordance with the viscosity of the fluid aerated and pumped.

Experiment has shown that so long as the profiles of the foil shaped contour, trough, leading edge and trailing edge are generally followed, the concept herein is not very sensitive to the particular profile used.

This being the case, we prefer the mirror image concept here disclosed because it is easy to generate, symmetrical around the center to save material, and seems to permit a flow continuity that does not generate dead or still spots in the resultant water flow.

For a given low input of energy, and an overall depth of 2' (needed for growing the algae), the distance between sparge lines was increased by one foot increments from 4' to 8'. At short intervals, the flow was excellent, but slowed down as the distance was increased to 8', allowing some deposition of algae to occur. We prefer a 6' distance as a compromise (the flow is good and the cost of plumbing is reduced).

For a given low input of energy and a given viscosity of the fluid, the distance between the water surface and the top of the crest of the profile seems a more critical parameter: With fresh water, 8" appeared to be a maximum (given the criteria by Ocean Genetics, to avoid creating dead spots). But sea water and seaweed (higher "viscosity") can tolerate a depth of 10".

What is claimed is:

1. In a liquid body having a liquid solution for aeration and pumping, a means for pumping said solution and a means defining a shallow bottom portion of said liquid body, said pumping means being integrally disposed in said shallow bottom portion, said pumping means comprising:

a foil shaped contour defined in said shallow bottom portion, said foil shaped contour having a trough defining the forward edge of said foil and defining the deepest portion of said shallow bottom;

a leading edge sloping up from said trough and defining in the first portion of said foil shaped bottom a shallow point adjacent the surface of said tank having sufficient depth for permitting liquid to flow over the surface thereof;

a trailing edge of said foil sloping downwardly from said leading edge to the level of said trough;

an air manifold placed in said trough for discharging a curtain of air from the bottom of said trough through said liquid to the surface of said liquid whereby said rising curtain of air entrains a rising wall of liquid to the surface and said liquid divides into a conventional eddy flowing away from the leading edge of said foil and to a translation pumping flow passing over the leading edge of said foil to the trailing edge of said foil whereby liquid is pumped over said foil from the leading to trailing edge.

2. The invention of claim 1 and wherein said shallow bottom portion has first and second foil shaped bottoms, said foils placed in series with the leading edge of one foil confronted to the trailing edge of the other foil; and each said trough on each said foil includes an air manifold.

3. In a tank having a suspended solution for aeration and pumping relative to the surface of said tank, an aerating and pumping means comprising a shallow bottom portion to said tank having a repeating foil shaped bottom, said repeating foil shaped bottom including at least two foils placed in series, each of said foils including:

a trough defining the forward edge of each said foil and defining the deepest portion of said shallow portion of said tank;

a leading edge sloping up from said trough and defining in the first portion of said foil shaped bottom a shallow point adjacent to the surface of said tank having sufficient depth permitting said liquid to flow over the surface thereof;

a trailing edge of a first foil being disposed immediately adjacent to the trough of a second foil, whereby said solution is directed from the trailing edge of said first foil through the trough and over the leading edge of the second foil;

said trailing edge of a first foil leading through a trough directly to the leading edge of the second foil;

an air manifold placed within the trough of each foil for discharging air from the bottom of said trough through said liquid to the surface of said liquid whereby said rising curtain of air entrains to the surface of said tank a rising wall of liquid and whereby said rising wall of liquid divides into a conventional eddy flowing away from the leading edge of each foil and into a translational pumping flow passing over the leading edge of each said foil whereby the translational pumping flow from the trailing edge of said first foil reinforces the conventional eddy flow of the back eddy from the second foil.

4. A process of aerating and pumping liquid across a shallow bottom tank comprising the steps of:

providing a shallow bottom having a foil shaped contour, said provided foil shaped contour including a trough defining the forward edge of said foil and defining the deepest portion of said bottom;

said provided foil shaped contour further defining a leading edge sloping up from said trough and defining in the first portion of said foil shaped bottom a shallow portion adjacent to the surface of said tank having sufficient depth permitting liquid to flow over the surface thereof;

said provided foil shaped contour further providing a trailing edge of said foil sloping downwardly from the leading edge to the level of said trough;

placing an air manifold within said trough immediately adjacent the leading edge for discharging air from the bottom of said trough through said liquid to the surface of said liquid; discharging air through said manifold whereby said rising curtain of air entrains a rising wall of liquid to the surface of said tank;

permitting the rising wall of liquid to divide whereby the wall of liquid divides said flow into a first flow and a second flow relative to said manifold and said trough, said first flow being a conventional eddy flowing away from the leading edge of said foil and said second flow being a translational pumping flow passing up and over the leading edge of said foil;

and permitting liquid to enter into the trough, flow over the leading edge of said foil and exit the trailing edge of said foil whereby liquid is pumped by said rising air.

* * * * *